US005663206A

United States Patent [19]

Ajoku et al.

[11] Patent Number: 5,663,206

[45] Date of Patent: Sep. 2, 1997

[54] SYNERGISTIC ANTIMICROBIAL COMPOSITION OF N-DECYL-N-ISONONYL-N,N-DIMETHYL AMMONIUM CHLORIDE AND ALKYLGUANIDINE COMPOUNDS

[75] Inventors: Kevin I. Ajoku, Imperial; Nancy J. Kapp, Glenshaw, both of Pa.

[73] Assignee: Calgon Corporation, Del.

[21] Appl. No.: 641,713

[22] Filed: May 2, 1996

[51] Int. Cl.[6] .......................... A01N 33/00; A01N 33/12; A01N 37/52

[52] U.S. Cl. .......................... 514/634; 504/158; 514/642

[58] Field of Search .................................... 514/642, 634; 504/158

[56] References Cited

U.S. PATENT DOCUMENTS

| | | | |
|---|---|---|---|
| 2,867,562 | 1/1959 | Lamb | 167/22 |
| 2,906,595 | 9/1959 | Pelcak et al. | 21/2.7 |
| 3,116,326 | 12/1963 | Lamb | 260/564 |
| 3,142,615 | 7/1964 | Wehner | 167/22 |
| 3,143,459 | 8/1964 | Marks et al. | 167/42 |
| 3,264,172 | 8/1966 | Regutti | 162/161 |
| 3,628,941 | 12/1971 | Marks | 71/67 |
| 4,745,132 | 5/1988 | Swered et al. | 514/634 |
| 5,290,805 | 3/1994 | Eastman | 514/642 |
| 5,457,083 | 10/1995 | Muia et al. | 504/128 |

*Primary Examiner*—Allen J. Robinson
*Attorney, Agent, or Firm*—D. R. Meyers; W. C. Mitchell

[57] ABSTRACT

Synergistic antimicrobial combinations comprising N-decyl-N-isononyl-N,N-dimethyl ammonium chloride and an alkylguanidine compound, preferably dodecylguanidine hydrochloride, are disclosed. Methods for inhibiting microbial growth using these synergistic antimicrobial combinations are also disclosed.

10 Claims, No Drawings

SYNERGISTIC ANTIMICROBIAL COMPOSITION OF N-DECYL-N-ISONONYL-N,N-DIMETHYL AMMONIUM CHLORIDE AND ALKYLGUANIDINE COMPOUNDS

BACKGROUND OF THE INVENTION

1. Field of the Invention

The present invention relates to synergistic antimicrobial compositions which are generally useful for inhibiting microbial growth wherever such microbial growth is found, for example in aqueous systems related to a wide variety of industrial applications. More particularly, the present invention relates to synergistic admixtures of N-decyl-N-isononyl-N,N-dimethyl ammonium chloride and alkylguanidine compounds. Methods for using the same are also disclosed.

2. Description of the Background Art

Both N-decyl-N-isononyl-N,N-dimethyl ammonium chloride, referred to herein as N-DIDAC, and alkylguanidine compounds, such as dodecylguanidine hydrochloride (DGH), are known individually as antimicrobial agents. The unexpected finding of the present invention is that they are synergistic when used in combination. As used herein, the terms "synergy" and "synergistic" refer to instances where the effectiveness of a composition comprising two or more biocides, such as N-DIDAC and DGH, exceeds the sum of the efficacies of the individual components taken alone. Thus, using a synergistic biocidal combination may allow for use of a lower overall concentration of biocide or the realization of an enhanced antimicrobial effect at a comparable dosage.

Alkylguanidine compounds, including dodecylguanidine hydrochloride, are known for their antimicrobial properties. For example, mineral acid or monocarboxylic acid salts of alkylguanidines and their use as antimicrobial agents are disclosed in U.S. Pat. Nos. 2,867,562, 2,906,595, 3,116,326, 3,142,615, 3,143,459, 3,264,172, and 3,628,941. The acid salts of dodecylguanidine are the best known and widely used compounds of the class. U.S. Pat. No. 4,745,132 discloses a synergistic mixture of N-dodecylguanidine and N-alkyl dimethyl benzyl ammonium halide and methods of using the same.

Likewise, the use of N-decyl-N-isononyl-N,N-dimethyl ammonium chloride and related compounds is known. The synergistic combination of N-DIDAC and DGH, however, is not taught or suggested in the art.

As used herein, the phrases "antimicrobial", "biocide", and "inhibiting microbial growth" refer to the killing of, the inhibition of, or the control of the growth of bacteria, yeast, mold and/or algae. A number of important industries have experienced serious adverse effects from the activity of such biological growth on the raw materials which they employ, in their process waters, on various components of their manufacturing processes, and in the finished products which they produce. Such industries include the paint, wood, textile, cosmetic, leather, tobacco, fur, rope, paper, pulp, plastics, fuel, oil, rubber, and machine industries.

It is contemplated that the synergistic admixture of N-DIDAC and alkylguanidine compounds as disclosed herein, and the methods for using the same, will be useful in virtually any aqueous system or on any article or product of manufacture in which inhibition of microbial growth is desired, absent compatibility problems. Suggested applications of the synergistic antimicrobial combinations of the present invention include, for example: inhibiting the growth of bacteria and fungi in aqueous paints, adhesives, latex emulsions, inks and joint cements; preserving wood; preserving cutting oils and metal working fluids; controlling slime-producing bacteria and fungi, including yeast and mold, in pulp and paper mills and cooling towers; as a spray or dip treatment for textiles and leather to prevent mold growth; as a component of anti-fouling paints to prevent adherence of fouling organisms; protecting paint films, especially exterior paints, from attack by fungi which occurs during weathering of the paint film; protecting processing equipment from slime deposits during manufacture of cane and beet sugar, food, foodstuffs and food additives; preventing microorganism buildup and deposits in air washer or scrubber systems and in industrial fresh water supply systems; controlling microorganism contamination in closed loop and recirculating water cooling systems; controlling microorganism contamination and deposits in oil field drilling fluids and muds, and in secondary petroleum recovery processes; preventing bacterial and fungal growth in paper coating processes which might adversely affect the quality of the paper coating; controlling bacterial and fungal growth and deposits during the manufacture of various specialty boards, e.g., cardboard, particle board and food grade board; preventing sap stain discoloration on freshly cut wood of various kinds; controlling bacterial and fungal growth in clay and pigment slurries of various types which are manufactured for later use in paper Coating and paint manufacturing and which are susceptible to degradation by microorganisms during storage and transport; as a hard surface disinfectant to prevent growth of bacteria and fungi on walls, floors, etc.; in swimming pools to prevent algal growth; and to control bacterial and fungal growth in various cosmetic products. It is further contemplated that the synergistic admixture of the present invention will be useful in various types of non-aqueous systems as well.

The synergistic antimicrobial composition disclosed in the present invention is particularly applicable to slime control in papermaking processes. The control of bacteria and fungi in pulp and paper mill water systems which contain aqueous dispersions of papermaking fibers in various consistencies is especially important. The uncontrolled buildup of slime produced by the accumulation of bacteria and fungi may cause off-grade production, decreased production due to down-time and greater cleanup frequency, increased raw material usage, and increased maintenance costs. The problem of slime deposits is especially critical in light of the widespread use of closed white water systems in the paper industry.

Another important area in which the antimicrobial compositions of the present invention are particularly useful is in the control of bacterial and fungal growth in clay and pigment slurries. These slurries comprise various clays (e.g., kaolin) and pigments (e.g., calcium carbonate and titanium dioxide) and usually are manufactured at a location separate from the end use application. This means that they are generally transported and stored for later use at the application site. Because of high quality standards for the paper and paint products in which such slurries are used, it is essential that these clay or pigment slurries have a very low microorganism count.

In addition, the synergistic combination of the present invention and methods of using the same have been found especially useful in controlling the harmful effects of microorganisms in water or aqueous media. Systems which utilize circulating water or aqueous media become infected with microorganisms and experience substantial impairment of their efficiency when deposits of the microorganisms build up in the system. The deposits coat the walls of tanks and other vessels and any machinery or processing equipment which is employed and create blockages in pipes and valves. The deposits also create discolorations and other imperfections in the products being produced, forcing costly shutdowns. Control of microorganisms in aqueous media is particularly important where there are dispersed particles or fines in the aqueous media, for example, dispersed cellulosic fibers and dispersed fillers and pigments in papermaking, and dispersed pigments in paint manufacture.

Accordingly, there remains a very real and substantial need for antimicrobial compositions capable of effectively controlling and/or inhibiting microbial growth in industrial aqueous systems and on articles of manufacture. Because of increasing environmental regulations, there is still a further need to provide biocidal compositions having enhanced antimicrobial effect which are effective in lower doses than historically used. Use of lower amounts of biocides has a favorable impact on the environment, and allows users to realize significant cost savings.

SUMMARY OF THE INVENTION

The present invention generally meets the above described needs by providing synergistic antimicrobial combinations comprising N-decyl-N-isononyl-N,N-dimethyl ammonium chloride and alkylguanidine compounds, particularly dodecylguanidine hydrochloride (DGH). The present invention also provides a method for inhibiting microbial growth in aqueous systems and on articles of manufacture prone to such growth comprising adding to said systems or applying to said articles an effective amount of a composition comprising: a) N-decyl-N-isononyl-N,N-dimethyl ammonium chloride; and b) an alkylguanidine.

As used herein, the term "effective amount" refers to that amount of a composition comprising N-DIDAC and an alkylguanidine compound necessary to achieve the desired level of inhibition or control of microbial growth in the aqueous system or on the article being treated.

DESCRIPTION OF THE INVENTION

The present invention is directed to a synergistic antimicrobial composition comprising: a) N-decyl-N-isononyl-N, N-dimethyl ammonium chloride; and b) an alkylguanidine compound, wherein the weight ratio of a) to b), on an active basis, ranges from about 1000:1 to 1:1000. The preferred alkylguanidine compound is dodecylguanidine hydrochloride (DGH). The present invention is further directed to a method for inhibiting microbial growth in an aqueous system or on an article of manufacture prone to such growth, which method comprises treating said system or said article with an effective amount of an antimicrobial composition comprising: a) N-decyl-N-isononyl-N,N-dimethyl ammonium chloride; and b) an alkylguanidine, wherein the weight ratio of a) to b), on an active basis, ranges from about 1000:1 to 1:1000. As used herein, the term "alkylguanidine compound" refers to any of the mineral acid salts, monocarboxylic acid salts, or other salts of alkyl guanidine including but not limited to the salts of dodecylguanidine.

In accordance with the present invention, the weight ratios of the two components of the synergistic combination are dictated by the dosage levels of each component which demonstrate synergism, based on 100% active ingredient, relative to each end use application. Typically, the weight ratio of component a), N-DIDAC, and component b), for example DGH, ranges from about 1000:1 to 1:1000 on an active basis, preferably from about 40:1 to 1:20, more preferably from about 6:1 to 1:12. As will be understood by one skilled in the art, however, the synergistic weight ratio of the two components generally varies to some extent depending on the application and the organism being controlled. For example, a higher ratio of N-DIDAC to DGH might be more effective in one application, while a higher ratio of DGH to N-DIDAC might be more effective in another application. The N-DIDAC/DGH composition has been found particularly effective against bacteria when used in a weight ratio of between about 5:1 to 1:3.

An effective mount of a synergistic combination of N-DIDAC and DGH should be added to the aqueous system being treated. At least about 0.1 parts per million (ppm), based on the weight of water in the system being treated, of the synergistic combination described above should be added. Preferably, between about 2 ppm and about 60 ppm of N-DIDAC and between about 10 ppm and 25 ppm of DGH, based on the weight of water in the system being treated, are added. More preferably, between about 2 ppm and 10 ppm of N-DIDAC and between about 2 ppm and 6 ppm of DGH, based on the weight of water in the system being treated, are added. It is well within the ordinary skill of one practicing in the art to determine the effective mount of biocide for a given system based on various system parameters including but not limited to the size of the system, pH of the system, the types of organisms present and the amount of control desired.

Likewise, an effective amount of a synergistic combination of N-DIDAC and DGH should be applied to the article of manufacture being treated. Generally, a solution of the synergistic antimicrobial combination described above having a concentration of at least 0.1 ppm is incorporated into, sprayed or poured onto, used to dip, or otherwise applied, for example by dipping or submersing, to the substrate being treated in order to prevent growth of bacteria, mold, yeast and algae. Again, it is well within the ordinary skill of one practicing in the art to determine the effective amount of biocide to apply to a given article of manufacture being treated and to determine suitable modes of application.

The active ingredients of the synergistic antimicrobial compositions of the present invention may also be used in diverse formulations: solid, including finely divided powders and granular materials; as well as liquid, such as solutions, emulsions, suspensions, concentrates, emulsifiable concentrates, slurries and the like, depending upon the application intended, and the formulation media desired. Further, when the synergistic antimicrobial combinations are liquid, they may be employed neat or may be incorporated into various formulations, both solid and liquid, as an adsorbate on suitable inert carriers such as talc, clays, diatomaceous earth and the like, or water and various organic liquids such as lower alkanols, kerosene, benzene, toluene, and other petroleum distillate fractions or mixtures thereof. N-DIDAC is commercially available in liquid form from Lonza Inc, Fair Lawn, N.J. as Bardac® 2170, which is 70% active N-DIDAC. DGH is commercially available from Calgon Corporation, Pittsburgh, Pa. in liquid form as Metasol® 350, which is 35% active DGH in a water and dipropylene glycol carrier.

To prepare a synergistic composition under this invention an effective amount of each active ingredient should be combined in a suitable carrier such as water, organic solvents and the like. The preparation of such a composition is within the ordinary skill of one practicing in the art.

It will also be understood by one skilled in the art that the synergistic antimicrobial combination disclosed herein may be used in combination with other antimicrobial materials. For example, the combination can be combined with other fungicides and bactericides in appropriate concentrations and in appropriate instances so as to combine the action of each to obtain particularly useful results. Such combinations might find particular application in the preparation of germicidal soaps, in the production of cosmetics and aqueous coatings and in combating paper mill microbial slime accumulations. It is clear also that the synergistic antimicrobial combination of the present invention can be combined with other algicidal agents as well.

In accordance with the present invention there is still further provided a method of inhibiting the growth of at least one of: bacteria, yeast, mold and algae. According to the methods of the present invention, this growth is inhibited in aqueous systems or on articles or products of manufacture prone to such growth. These methods comprise adding to the aqueous system or treating the article or product containing said bacteria, yeast, mold and/or algae with an effective mount of a synergistic combination of N-DIDAC and an alkylguanidine compound such as DGH. This addition can be accomplished either by simple addition of N-DIDAC and DGH together as a single admixture, or by addition of the two components separately. Such separate administration can either be at the same time or at different times. The net effect will be the same—the system, article or product being treated will ultimately have incorporated therein or have applied thereto the desired dosage concentration of each component.

Further, the compositions of the present invention are believed to be effective irrespective of the method of application. For example, the antimicrobial compositions described herein can be added to a system being treated via a low level, continuous feed practice, a semi-continuous feed practice or through slug feeding. All of these feeding practices will be familiar to one having ordinary skill in the art. Slug feeding is particularly effective and therefore is a preferred manner of employing the methods of the present invention. This type of feed allows the user to monitor the microorganism concentration in the system and feed product only when microorganism concentrations increase. The user realizes a cost savings by feeding an effective amount of N-DIDAC and DGH only when needed.

As noted above, the present invention is based upon the discovery that use of N-DIDAC in conjunction with alkylguanidine compounds produces synergistic results and is effective in controlling the growth of bacteria, yeast, mold and algae in a variety of industrial and other applications. The utility of the synergistic antimicrobial combination disclosed herein derives from its versatility both in the numerous industries in which it can be applied, as well as the numerous microorganisms against which it is effective. In particular, the large economic losses in papermaking operations caused by the accumulation of bacterial and fungal slimes in various parts of the system can be eliminated to a significant extent by use of the synergistic combination described herein.

The superior antimicrobial activity of the synergistic antimicrobial combination of N-DIDAC and DGH has been confirmed using standard laboratory techniques. The antimicrobial combination has been found effective, for example, in inhibiting bacterial growth including but not limited to *Klebsiella pneumoniae* and *Escherichia coli* and has been found to be particularly effective against *Pseudomonas aeruginosa*. The combination is also believed to be effective against other aerobic bacteria, such as *Bacillus* sp., *Staphylococcus* sp., *Flavobacterium* sp., *Enterobacter* sp., and *Xanthomonas* sp., anaerobic bacteria, other fresh water organisms such as filamentous bacteria, fungi including but not limited to various species of *Candida* and *Saccharomyces* and white and pink yeasts, and various species of algae.

EXAMPLES

The following examples are set forth to illustrate the present invention and should not be construed as limiting the invention in any way.

Example I

The biocidal efficacy in microtiter tests of the antimicrobial composition of the present invention is demonstrated below. Three different bacterial strains, *Klebsiella pneumoniae, Escherichia coli, Pseudomonas aeruginosa*, as well as a mixture of all three of the strains, were used.

Each of the three bacteria were separately grown on Standard Methods Agar (STM) plates and incubated at 37° C. for a period of between about 24–48 hours. The bacteria were then swabbed from their respective STM plates and suspended in 50 ml of double strength trypticase soy broth (2XTSB) and incubated again at 37° C. for 24 hours; each organism was incubated in a separate tissue culture flask. The 2XTSB was prepared by mixing about 30 grams of trypticase soy broth powder in about 1000 ml of deionized water which had been autoclave sterilized. Following the 24 hour incubation of each of the organism suspensions, the suspensions were diluted in a ratio of 1:10 with additional 2XTSB. Samples from each of these diluted cultures were then used in the microtiter test. To prepare the mix of all three of the organisms, an equal amount, approximately 10 ml, of each of the diluted cultures was mixed together in a separate tissue culture flask. Samples from this mixture were then used in the microtiter test.

An 8X stock solution of DGH to use in combination with N-DIDAC was prepared by dissolving about 3.2 grams (g) of 24.7% active DGH in about 100 ml of deionized water. A 4X stock solution of DGH to use in combination with N-DIDAC was prepared in the same manner only using 0.0162 g of DGH. A 4X stock solution of DGH to use alone was prepared in the same manner only using 1.6 g of DGH. The DGH used in the examples was obtained from Calgon Corporation, Pittsburgh, Pa., as Metasol® 600HF. An N-DIDAC 8X stock solution to use in combination with DGH was prepared by dissolving about 1.0 g of about 80% active Bardac 2180 in about 100 ml with deionized water. A 4X stock solution of N-DIDAC to use in combination with DGH was prepared in the same manner only using 0.005 g Bardac 2180. The 4x stock solution of N-DIDAC to use alone was prepared in the same manner only using 0.5 g of Bardac 2180. The Bardac 2180 was obtained from Lonza, Inc., Fair Lawn, N.J.

Eight microtiter plates were used in the example, each microtiter plate having 8 rows, A—H, and 12 columns, 1–12. The amount of each biocide in each well of the eight plates is depicted below.

TABLE 1

AMOUNT OF EACH BIOCIDE IN WELLS OF MICROTITER PLATE 1–8

| PLATE | | COLUMN CONCENTRATIONS (ppm Active) | | | | | | | | | | | |
|---|---|---|---|---|---|---|---|---|---|---|---|---|---|
| # | BIOCIDE | 1 | 2 | 3 | 4 | 5 | 6 | 7 | 8 | 9 | 10 | 11 | 12 |
| 1, 5 | N-DIDAC (4X) | 1000 | 500 | 250 | 125 | 62 | 31 | 16 | 8 | 4 | 2 | – | + |
| | DGH (8X) | 10 | 10 | 10 | 10 | 10 | 10 | 10 | 10 | 10 | 10 | – | + |
| 2, 6 | N-DIDAC (8X) | 10 | 10 | 10 | 10 | 10 | 10 | 10 | 10 | 10 | 10 | – | + |
| | DGH (4X) | 1000 | 500 | 250 | 125 | 62 | 31 | 16 | 8 | 4 | 2 | – | + |
| 3, 7 | N-DIDAC (8X) | 0 | 0 | 0 | 0 | 0 | 0 | 0 | 0 | 0 | 0 | – | + |
| | DGH (8X) | 1000 | 500 | 250 | 125 | 62 | 31 | 16 | 8 | 4 | 2 | – | + |
| 4, 8 | N-DIDAC (4X) | 1000 | 500 | 250 | 125 | 62 | 31 | 16 | 8 | 4 | 2 | – | + |
| | DGH (4X) | 0 | 0 | 0 | 0 | 0 | 0 | 0 | 0 | 0 | 0 | – | + |

As is illustrated in the table above, the amount of DGH in the wells of plates 1 and 5 and the amount of N-DIDAC in the wells of plates 2 and 6 were varied in a serial dilution series ranging from 1000 ppm active to 2 ppm active while the other component's concentration was kept at 10 ppm active; plates 3 and 7 represented use of DGH alone, while plates 4 and 8 represented the use of N-DIDAC alone. Plates 3 and 4, and 7 and 8 were used to determine the minimum amount of each biocide which, when used alone, would inhibit microbial growth. No biocide was added to the wells of column 12 in any of the plates, which represented an organism control, or positive control. This positive control was run to ensure that the organisms were capable of growing in the environment provided. No bacteria were added to the wells of column 11 in any of the plates, which represented a broth control, or a negative control. This was done to ensure that there was no contamination of the plates. In each of the 8 microtiter plates *Pseudomonas aeruginosa* was added to rows A and B, *Klebsiella pneumoniae* to rows C and D, *Escherichia coli* to rows E and F, and the mix of all three bacteria to rows G and H.

Plates 1–4 were used to determine the minimum inhibitory concentration (MIC) for each biocide combination against each bacteria strain. The MIC is the least amount of biocide needed to prevent growth in the well, with growth being defined as a turbidity in the medium or a "pellet" of cells which came out of the medium and settled at the bottom of the well.

Plates 5–8 were then subcultured from plates 1–4, respectively, at 24 hours following biocide addition. Subculturing was done to determine the minimum biocidal concentration (MBC). The MBC is the lowest concentration of biocide that results in no growth after subculturing and subsequent incubation.

All of the microtiter plates including the MIC plates and the MBC plates were incubated for 24 hours at 37° C. Following the 24 hour incubation period, the presence or absence of growth in each well of the plates was determined. Growth in the microtiter plates was determined with a Dynatech MR-5000 microplate reader, available from Dynatech Laboratories, Chantilly, Va., the use of which will be familiar to one having ordinary skill in the art. The presence or absence of growth in each well, along with the concentration of biocide in each well, was then used to determine the synergistic properties of the biocide combinations. The synergistic properties were evaluated by determining the Kull value, or K value; the K value was determined for each of the bacteria tested. The method for calculating K value is well known to those skilled in the art. In this example, the K value was determined by the following formula:

$$K = \frac{[DGH] \text{ In Combination}}{[DGH] \text{ Alone}} + \frac{[N\text{-}DIDAC] \text{ In Combination}}{[N\text{-}DIDAC] \text{ Alone}}$$

where "[DGH] In Combination" means the concentration of DGH which, when used in combination with N-DIDAC, resulted in inhibition of microbial growth;

"[N-DIDAC] In Combination" means the concentration of N-DIDAC which, when used in combination with DGH, resulted in inhibition of microbial growth;

"[DGH] Alone" means the concentration of DGH which, when used alone, resulted in inhibition of microbial growth; and "[N-DIDAC] Alone" means the concentration of the N-DIDAC which, when used alone, resulted in inhibition of microbial growth.

A K value of less than 1 indicates synergy between the two biocides, a K value of greater than 1 indicates antagonism between the two biocides, and a K value equal to 1 indicates an additive effect of the two biocides.

The K values determined for each of the organisms used in the example are recorded in Tables 2 through 5.

TABLE 2

"K" VALUES OF PLATE 1 (MIC)

| Organism | [DGH] Alone, ppm | [N-DIDAC] Alone, ppm | [DGH] In Combination, ppm | [N-DIDAC] In Combination, ppm | K Value | Weight Ratio N-DIDAC: DGH |
|---|---|---|---|---|---|---|
| *Pseudomonas aeruginosa* | 47 | 31 | 10 | 31 | 1.2 | 3:1 |
| *Klebsiella pneumoniae* | 8 | 12 | <10 | <2 | 1.4 | 1:5 |
| *Escherichia coli* | 4 | 12 | <10 | <2 | 2.7 | 1:5 |
| Mixture of above three 31 | 31 | 31 | 10 | 30 | 1.3 | 3:1 |

TABLE 3

"K" VALUES OF PLATE 2 (MIC)

| Organism | [DGH] Alone, ppm | [N-DIDAC] Alone, ppm | [DGH] In Combination, ppm | [N-DIDAC] In Combination, ppm | K Value | Weight Ratio N-DIDAC: DGH |
|---|---|---|---|---|---|---|
| *Pseudomonas aeruginosa* | 47 | 31 | 24 | 10 | 0.83 | 1:2.4 |
| *Klebsiella pneumoniae* | 8 | 12 | <2 | <10 | 1.1 | 5:1 |
| *Escherichia coli* | 4 | 12 | <2 | <10 | 1.3 | 5:1 |
| Mixture of above three | 31 | 31 | 24 | 10 | 1.1 | 1:2.4 |

TABLE 4

"K" VALUES OF PLATE 5 (MBC)

| Organism | [DGH] Alone, ppm | [N-DIDAC] Alone, ppm | [DGH] In Combination, ppm | [N-DIDAC] In Combination, ppm | K Value | Weight Ratio N-DIDAC: DGH |
|---|---|---|---|---|---|---|
| *Pseudomonas aeruginosa* | 125 | 31 | 10 | 62 | 1.4 | 6.2:1 |
| *Klebsiella pneumoniae* | 8 | 12 | <10 | <2 | <1.4 | 1:5 |
| *Escherichia coli* | 8 | 12 | <10 | <2 | <1.4 | 1:5 |
| Mixture of above three | 94 | 31 | 10 | 62 | 0.76 | 6.2:1 |

TABLE 5

"K" VALUES OF PLATE 6 (MBC)

| Organism | [DGH] Alone, ppm | [N-DIDAC] Alone, ppm | [DGH] In Combination, ppm | [N-DIDAC] In Combination, ppm | K Value | Weight Ratio N-DIDAC: DGH |
|---|---|---|---|---|---|---|
| *Pseudomonas aeruginosa* | 125 | 31 | 156 | 10 | 1.5 | 1:15.6 |
| *Klebsiella pneumoniae* | 8 | 12 | <2 | <10 | 0.88 | 5:1 |
| *Escherichia coli* | 8 | 12 | <2 | <10 | 0.88 | 5:1 |
| Mixture of above three | 94 | 31 | 94 | 10 | 1.1 | 1:9.4 |

As can be seen from the results of Table 2–5, synergy was demonstrated against all three organisms tested, as well as the mix of these three organisms.

Example II

Example I was repeated using different concentrations of N-DIDAC and DGH. N-DIDAC was tested at concentrations of 200, 100, 50, 25, 12.5, 6.2, 3.1, 1.6, 0.8 and 0.4 ppm, while the amount of DGH was held constant at 2 ppm. DGH was tested at the same concentrations while the amount of N-DIDAC was held constant at 2 ppm. Use of N-DIDAC alone and DGH alone was also tested in a serial dilution ranging from 200 ppm to 0.4 ppm. Results are presented in Tables 6–9 below.

TABLE 6

"K" VALUES OF PLATE 1 (MIC)

| Organism | [DGH] Alone, ppm | [N-DIDAC] Alone, ppm | [DGH] In Combination, ppm | [N-DIDAC] In Combination, ppm | K Value | Weight Ratio N-DIDAC: DGH |
|---|---|---|---|---|---|---|
| *Pseudomonas aeruginosa* | 25 | 25 | 2 | 50 | 2.1 | 25:1 |
| *Klebsiella pneumoniae* | 6.2 | 12.5 | 2 | 9.4 | 1.1 | 4.7:1 |
| *Escherichia coli* | 3.1 | 12.5 | 2 | 3.3 | 0.91 | 1.6:1 |
| Mixture of above three | 25 | 25 | 2 | 50 | 2.1 | 25:1 |

TABLE 7

"K" VALUES OF PLATE 2 (MIC)

| Organism | [DGH] Alone, ppm | [N-DIDAC] Alone, ppm | [DGH] In Combination, ppm | [N-DIDAC] In Combination, ppm | K Value | Weight Ratio N-DIDAC: DGH |
|---|---|---|---|---|---|---|
| *Pseudomonas aeruginosa* | 25 | 25 | 25 | 2 | 1.1 | 1:12.5 |
| *Klebsiella pneumoniae* | 6.2 | 12.5 | 6.2 | 2 | 1.2 | 1:3.1 |
| *Escherichia coli* | 3.1 | 12.5 | 6.2 | 2 | 1.6 | 1:2.3 |
| Mixture of above three | 25 | 25 | 25 | 2 | 1.1 | 1:12.5 |

TABLE 8

"K" VALUES OF PLATE 5 (MBC)

| Organism | [DGH] Alone, ppm | [N-DIDAC] Alone, ppm | [DGH] In Combination, ppm | [N-DIDAC] In Combination, ppm | K Value | Weight Ratio N-DIDAC: DGH |
|---|---|---|---|---|---|---|
| *Pseudomonas aeruginosa* | 50 | 125 | 2 | 75 | 0.64 | 37.5:1 |
| *Klebsiella pneumoniae* | 6.2 | 12.5 | 2 | 9.4 | 1.1 | 4.7:1 |
| *Escherichia coli* | 9.4 | 12.5 | 2 | 4.6 | 0.58 | 2.3:1 |
| Mixture of above three | 37.5 | 50 | 2 | 50 | 1.0 | 25:1 |

TABLE 9

"K" VALUES OF PLATE 6 (MBC)

| Organism | [DGH] Alone, ppm | [N-DIDAC] Alone, ppm | [DGH] In Combination, ppm | [N-DIDAC] In Combination, ppm | K Value | Weight Ratio N-DIDAC: DGH |
|---|---|---|---|---|---|---|
| *Pseudomonas aeruginosa* | 50 | 125 | 37.5 | 2 | 0.77 | 1:18.75 |
| *Klebsiella pneumoniae* | 6.2 | 12.5 | 6.2 | 2 | 1.2 | 1:3.1 |
| *Escherichia coli* | 9.4 | 12.5 | 6.2 | 2 | 0.82 | 1:3.1 |
| Mixture of above three | 37.5 | 50 | 25 | 2 | 0.71 | 1:12.5 |

What is claimed is:

1. A synergistic antimicrobial combination comprising:

a) N-decyl-N-isononyl-N,N-dimethyl ammonium chloride; and b) an alkylguanidine compound; wherein the weight ratio of a) to b), on an active basis, ranges between about 40:1 and 1:20 and wherein said alkylguanidine compound is dodecylguanidine hydrochloride.

2. A method of inhibiting microbial growth in an aqueous system which comprises adding to said system an effective amount of a synergistic antimicrobial combination comprising:

a) N-decyl-N-isononyl-N,N-dimethyl ammonium chloride; and b) an alkylguanidine compound; wherein the weight ratio of a) to b), on an active basis, ranges between about 40:1 and 1:20 and wherein said alkylguanidine compound is dodecylguanidine hydrochloride.

3. The method of claim 2 wherein the N-decyl-N-isononyl-N,N-dimethyl ammonium chloride and alkylguanidine compound are added together as a single composition to the system being treated.

4. The method of claim 2 wherein the N-decyl-N-isononyl-N,N-dimethyl ammonium chloride and alkylguanidine compound are added separately to the system being treated.

5. The method of claim 2 wherein at least 0.1 ppm of the synergistic antimicrobial composition is added to the system being treated.

6. The method of claim 5 wherein between about 10 ppm and 2 ppm N-decyl-N-isononyl-N,N-dimethyl ammonium chloride and between about 2 ppm and 6 ppm dodecylguanidine hydrochloride are added to the system being treated.

7. A method of inhibiting microbial growth on an article of manufacture which comprises applying to said article an effective amount of a synergistic antimicrobial combination comprising:

a) N-decyl-N-isononyl-N,N-dimethyl ammonium chloride; and b) an alkylguanidine compound; wherein the weight ratio of a) to b), on an active basis, ranges between about 40:1 and 1:20 and wherein the alkylguanidine compound is dodecylguanidine hydrochloride.

8. The method of claim 7 wherein the N-decyl-N-isononyl-N,N-dimethyl ammonium chloride and alkylguanidine compounds are applied together as a single composition to the article being treated.

9. The method of claim 7 wherein the N-decyl-N-isononyl-N,N-dimethyl ammonium chloride and alkylguanidine compound are applied separately to the article being treated.

10. The method of claim 7 wherein said synergistic antimicrobial composition has a concentration of at least 0.1 ppm.

* * * * *